(12) United States Patent
Boboltz (10) Patent No.: US 11,678,929 B2
(45) Date of Patent: Jun. 20, 2023

(54) ASSEMBLY FOR SEQUENTIALLY PERCUTANEOUSLY APPLYING AN ELECTRODE AND AN ANESTHETIC TO TISSUE

(71) Applicant: Stryker Corporation, Kalamazoo, MI (US)

(72) Inventor: David R. Boboltz, Kalamazoo, MI (US)

(73) Assignee: Stryker Corporation, Kalamazoo, MI (US)

(*) Notice: Subject to any disclaimer, the term of this patent is extended or adjusted under 35 U.S.C. 154(b) by 1080 days.

(21) Appl. No.: 16/403,942

(22) Filed: May 6, 2019

(65) Prior Publication Data
US 2019/0254739 A1 Aug. 22, 2019

Related U.S. Application Data

(63) Continuation of application No. 15/183,092, filed on Jun. 15, 2016, now abandoned, which is a
(Continued)

(51) Int. Cl.
*A61B 18/14* (2006.01)
*A61M 5/32* (2006.01)
(Continued)

(52) U.S. Cl.
CPC .............. *A61B 18/1477* (2013.01); *A61B 2017/00477* (2013.01); *A61B 2018/00434* (2013.01);
(Continued)

(58) Field of Classification Search
CPC ...... A61B 18/1477; A61B 2017/00477; A61B 2018/00434; A61B 2018/00577;
(Continued)

(56) References Cited

U.S. PATENT DOCUMENTS

3,682,162 A 8/1972 Colyer
3,727,613 A 4/1973 Sorenson et al.
(Continued)

*Primary Examiner* — Linda C Dvorak
*Assistant Examiner* — Lindsay Regan Lancaster
(74) *Attorney, Agent, or Firm* — Howard & Howard Attorneys PLLC (57) ABSTRACT

An assembly for performing an electrosurgical procedure. A cannula includes a cannula hub defining a middle bore having a smaller diameter than a proximal bore. An electrode includes an electrode head having an outer diameter smaller than the proximal bore and greater than the middle bore. A syringe includes a syringe head having a length sufficient to extend past the proximal bore, and an outer diameter sized to engage the middle bore to form an annular seal at an interface between the syringe and the cannula. A step may define a transition surface between the proximal bore and the middle bore, and at least one notch may be within the step to maintain fluid communication between the middle bore and the proximal bore when the electrode head is engaging the step. The cannula head may include first and second locking features configured to engage the syringe and electrode, respectively.

8 Claims, 4 Drawing Sheets

Related U.S. Application Data continuation of application No. PCT/US2014/070703, filed on Dec. 17, 2014.

(60) Provisional application No. 61/917,604, filed on Dec. 18, 2013.

(51) Int. Cl.
   *A61B 17/00* (2006.01)
   *A61B 18/00* (2006.01)

(52) U.S. Cl.
   CPC .............. *A61B 2018/00577* (2013.01); *A61B 2018/1425* (2013.01); *A61M 5/3293* (2013.01); *A61M 2202/048* (2013.01)

(58) Field of Classification Search
   CPC ........ A61B 2018/1425; A61M 5/3293; A61M 2202/048
   See application file for complete search history.

(56) References Cited

U.S. PATENT DOCUMENTS

| | | |
|---|---|---|
| 5,002,538 A | 3/1991 | Johnson |
| 6,039,302 A | 3/2000 | Cote, Sr. et al. |
| 6,110,128 A | 8/2000 | Andelin et al. |
| 6,171,285 B1* | 1/2001 | Johnson ................. A61M 5/322 604/110 |
| 6,298,256 B1 | 10/2001 | Meyer |
| 6,500,153 B1* | 12/2002 | Sheppard .............. A61M 5/346 604/188 |
| 7,041,050 B1 | 5/2006 | Ronald |
| 7,713,256 B2 | 5/2010 | Brimhall et al. |
| 7,713,257 B2 | 5/2010 | Brimhall et al. |
| 7,776,035 B2 | 8/2010 | Rick et al. |
| 7,918,852 B2 | 4/2011 | Tullis et al. |
| 2004/0064107 A1* | 4/2004 | Lo .......................... A61M 5/348 604/240 |
| 2005/0043709 A1 | 2/2005 | Brimhall et al. |
| 2007/0179454 A1* | 8/2007 | Ziman ................... A61M 5/158 604/249 |
| 2010/0030146 A1* | 2/2010 | Kakish .................. A61M 5/504 604/110 |
| 2011/0160723 A1 | 6/2011 | Tullis et al. |
| 2011/0251597 A1 | 10/2011 | Bharadwaj et al. |
| 2012/0016316 A1 | 1/2012 | Zhuang et al. |
| 2013/0267980 A1 | 10/2013 | Torrie et al. |
| 2016/0022924 A1* | 1/2016 | Iwase ................... A61M 5/3287 604/241 |
| 2016/0287321 A1 | 10/2016 | Boboltz |
| 2017/0050041 A1* | 2/2017 | Cosman .................... A61N 1/36 |

* cited by examiner

ASSEMBLY FOR SEQUENTIALLY PERCUTANEOUSLY APPLYING AN ELECTRODE AND AN ANESTHETIC TO TISSUE

CROSS REFERENCE TO RELATED APPLICATIONS

This application is a continuation of copending U.S. application Ser. No. 15/183,092, filed Jul. 15, 2016, which is a continuation of PCT Application No. PCT/US2014/070703, filed Dec. 17, 2014, which claims priority to and all the benefits of U.S. Provisional Application No. 61/917,604, the contents of each are hereby incorporated by reference in their entireties.

FIELD OF THE INVENTION

This invention relates generally to an assembly for percutaneously applying an electrode and fluid to tissue. The assembly of this invention includes features that facilitate the rapid and precise positioning of the electrode.

BACKGROUND OF THE INVENTION

In some medical procedures it is desirable to both apply an electrical current and a fluid to the same target location within the body of the patient. One such procedure in which these steps are performed is a nerve ablation procedure. In a nerve ablation procedure, the nerve subjected to the procedure is ablated, essentially removed. As a result of the ablation process, the nerve no longer functions as a carrier for neurological signals. A nerve ablation is performed in some situations when the patient's neurological system continually transmits signals to the brain that provide the perception that that a limb or other portion of the patient is in pain. To eliminate the transmission of these signals, it is a known practice to ablate the nerves that continually transmit the pain signals to the brain.

A first step of a nerve ablation procedure is to insert a cannula into the patient. The distal end of the cannula is located in close proximity to the nerve targeted for the ablation procedure. An electrode is inserted in the cannula. A low power current, called a stimulating current, is then sourced from the electrode to the tissue adjacent the end of the cannula. The reaction of the patient to this current is monitored. More specifically, the practitioner monitors the reaction of the patient to determine how close the electrode is to the nerve that should be ablated. As part of this process, the cannula, with the electrode still inside, is typically repositioned. Once it is determined that the cannula and electrode are correctly positioned, the electrode is removed. The distal end of a syringe filled with a fluid, specifically an anesthetic, is inserted in the hub located at the proximal end of the cannula. The anesthetic is introduced through the cannula to the nerve and tissue surrounding the nerve. The syringe is withdrawn and the electrode reinserted into the cannula. A current is again sourced from the electrode. This current, referred to as an ablating current, is at a much higher level than stimulating current. Specifically, the ablating current is at level at which, when applied to the nerve, causes the ablation of the nerve. During this process the anesthetic reduces, if not completely blocks, the pain signals generated during the application of this relatively high current to the tissue.

As mentioned above, the cannula employed in this type of assembly includes a hub. The hub has a relatively large diameter bore in which a complementary head of the electrode and head of syringe are alternatingly fitted. A problem with many known versions of these assemblies is that it has proven difficult to, when the electrode is reinserted into the cannula, to perform the ablation step, position the distal end of the electrode so it extends the same distance out of the cannula as it did during the stimulating step. Having to take the time to so precisely reposition the electrode can add to the overall time it takes to perform a nerve ablation procedure.

SUMMARY OF THE INVENTION

This invention relates to a new and useful assembly for interchangeably inserting an electrode into and coupling a syringe to a cannula. The assembly of this invention is designed so that each time the electrode is inserted in the cannula, the distal end of the electrode extends out of the cannula essentially the same distance as it did during the previous insertions.

A further feature of this invention that essentially a zero force is employed to insert the electrode into or withdraw the electrode from the cannula. While essential zero force is employed to insert or withdraw the electrode, the assembly of this invention includes a means for releasably holding the electrode to the cannula.

In one version of this invention, the cannula includes a hub that is formed with a number of contiguous bores. The bores form a through path to the tube portion of the cannula that extends distally from the hub. The cannula is further formed so that the cannula has a stop. In some versions of the invention, a lip or tabs that extend outwardly around the open end of the proximal most bore function as the stop. In some versions of the invention, the stop projects into at least one of the bores. In some versions of this invention, this stop is a step that forms the transition between two contiguous bores in the cannula. The cannula is further formed so that the proximal bore with which the stop is formed is dimensioned to facilitate the slip fitting of the electrode into the bore. The electrode is slip fitted into the bore until the electrode abuts the stop.

One or more of the bores proximal to the stop is dimensioned to receive the head of the syringe. This bore is located distal to the proximal end bore, the bore dimensioned to receive the head of the electrode.

A further feature of the invention is that cannula is formed with a feature configured to releasably engage the electrode. Typically, this feature is disposed in the proximally located bore, the bore in which the electrode is disposed. In many versions of the invention the proximal bore has a constant diameter. In many versions of the invention, the feature configured to releasably engage the electrode projects into the proximal bore.

In another version of the invention, the cannula has two proximal end bores. A first one of the bores is dimensioned to receive the head of the electrode. A second one of the proximal end bores is dimensioned to receive the head of the syringe. Both the electrode and syringe can be simultaneously removably attached to the cannula of this version of the invention.

BRIEF DESCRIPTION OF THE DRAWINGS

The invention is pointed out with particularity in the claims. The above and further features and advantages of this invention are understood from the following detailed description taken in conjunction with the accompanying drawings in which:

DETAILED DESCRIPTION

Figure 1:
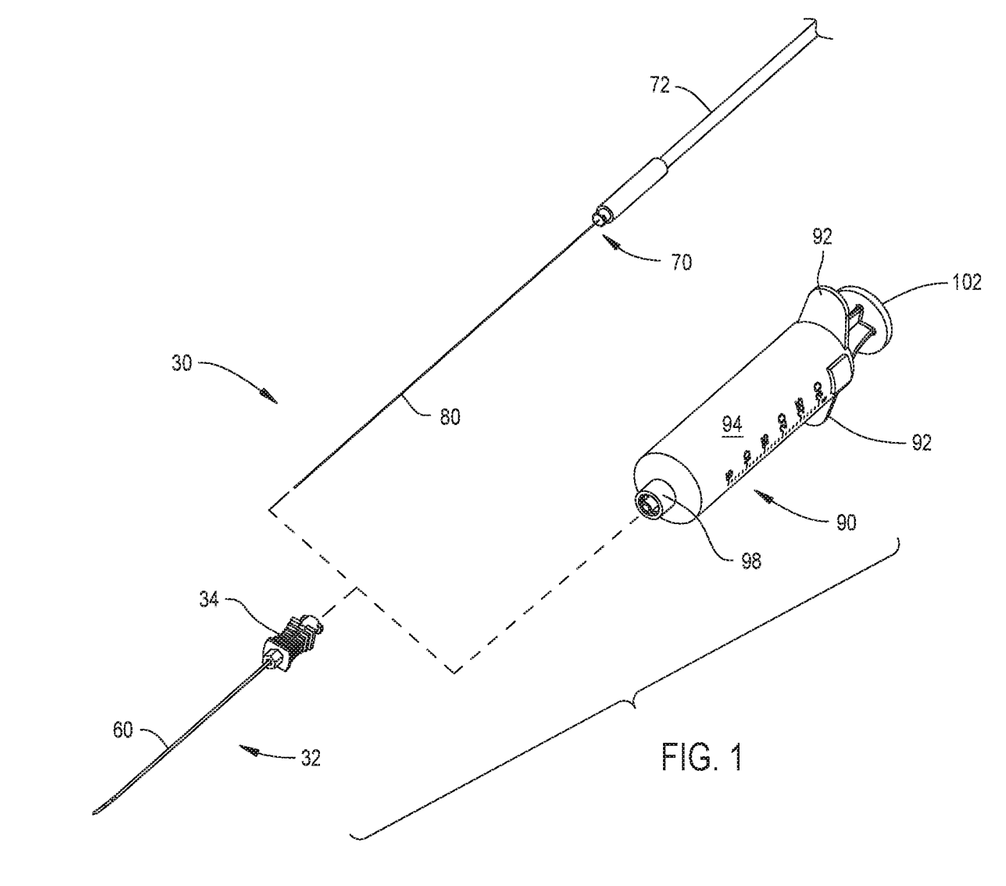
FIG. 1 depicts the components of the assembly of this invention.

FIG. 1 depicts the basic components of an assembly 30 of this invention. These components include a cannula 32. Cannula 32 is inserted percutaneously into the patient to provide a portal that opens into the space adjacent the tissue against which the current is to be applied. An electrode 70, also part of assembly 30, is inserted into the cannula 32. The electrode 70 is the device that sources the current to the tissue. Assembly 30 also includes a syringe 90. Syringe 90 is the source of fluid that is introduced into the tissue. This fluid is typically an anesthetic.

Figures 2, 3, 4, 5A:
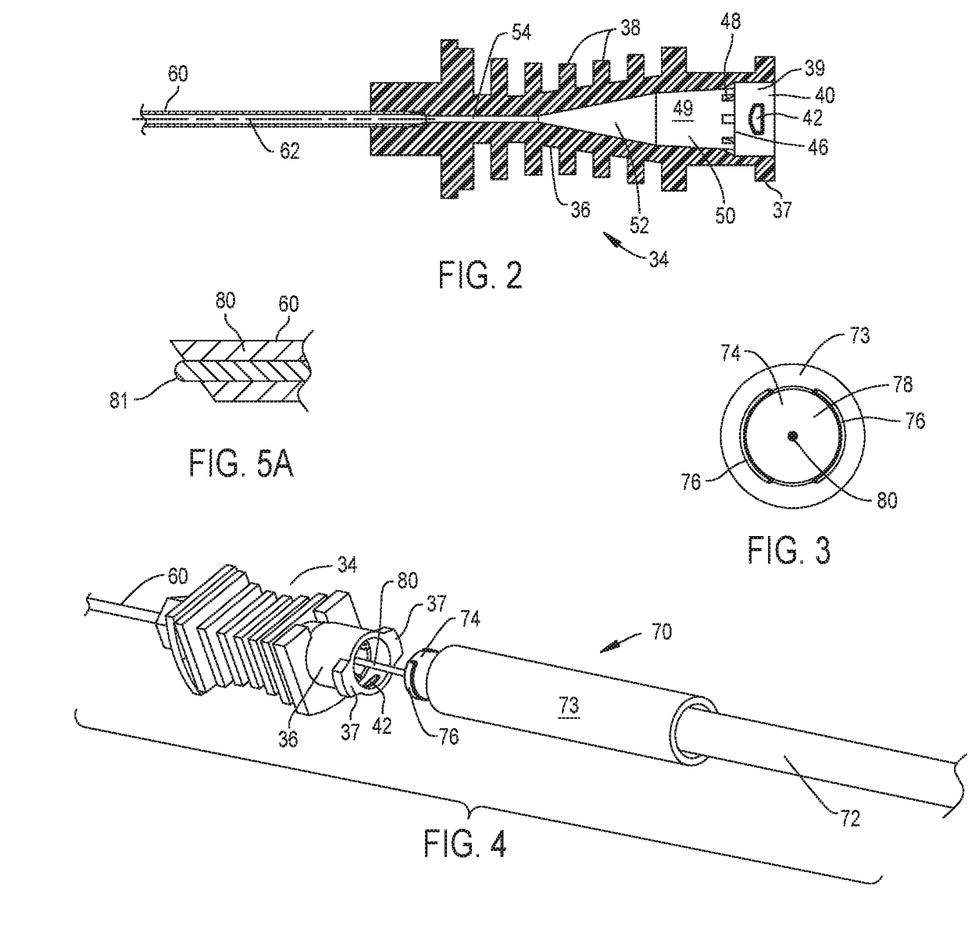
FIG. 2 is a cross sectional view of the proximal portion of the cannula of this invention.
FIG. 3 is a plan view of the distal end face of the head of an electrode of this invention.
FIG. 4 is a perspective view of the insertion of an electrode into the cannula.
FIG. 5A is a an enlarged cross sectional view of the distal ends of the cannula and electrode.

As seen by reference to FIGS. 1 and 2, cannula 32 includes a hub 34 from which a tube 60 extends distally forward. ("Distal" is to mean away from the practitioner using assembly 30, towards the percutaneous target site to which the assembly is applied. "Proximally" is understood to mean towards the practitioner holding the assembly, away from the site to which the assembly 30 is applied.) Hub 34 is dimensioned to be held between two fingers. The hub 34 is formed from a soft plastic such as an ABS plastic or Nylon, or other material that has a degree of flexibility or compliancy. Hub 34 has a body 36 that, while generally circular in cross section, has an outer diameter that extending from the proximal to distal ends of the body, decreases. A number of parallel fins 38 extend outwardly from the hub body 36. The outer surfaces of the fins 38 are the portions of the cannula 32 held by the practitioner to position the cannula. At the most proximal end of the body 36 two diametrically opposed tabs 37 (one identified) project radially outwardly. There is a separation between tabs 37 and the proximalmost fins 38.

Hub body 36 is further formed to have a number of contiguous bores that collectively form a through path that extend proximally to distally along the longitudinal axis of the body. A proximal bore 40 extends distally forward from the proximal end of the body 36. The hub 34 is shaped so that the proximal bore 40 has a diameter that is constant along the length of the bore. Cannula 32 is further formed so that at least one, if not plural, ribs 42 project radially inwardly from the inner circular wall 39 of the hub 34 that defines bore 40. While not apparent from the drawings, in the described version of the invention there are two ribs 42, the ribs being arcuately spaced apart from each other. In this version of the invention, each rib subtends an arc of between 30 and 90°. The opposed sides of the ribs are thus spaced between 90 and 150° from each other. It is a further feature of cannula 32 that the ribs 42 terminate at a location that is spaced proximally away from the distal end of the proximal bore 40. In the illustrated version of the invention proximal end of each rib 42 is located distally forward of the proximal end opening into the bore 40.

While not identified, it can be seen that each rib 42 has a distally directed face. Two wing faces taper proximally away from the opposed sides of the distally directed face. A side surface extends proximally away from the free end of each wing face. A rear face extends between the spaced apart side faces.

Proximal bore 40 opens into first middle bore 50. Hub body 36 is shaped so that the proximal end of middle bore 50 is smaller in diameter than the adjacent distal end of proximal 40. In some versions of the invention, the diameter of the proximal end of middle bore 50 is approximately 0.2 to 1.5 mm less than the diameter of proximal bore 40. In most versions of the invention the difference in the diameters of the two bores 40 and 50 is at least 0.6 mm. This difference in bore diameter with the hub 32 means that, within the hub body, there is a step 46. Step 46 defines the distal end of proximal bore 40 and extends radially inwardly from the outer perimeter of the proximal bore. The step 46 has an inner perimeter that defines the outer perimeter of the proximal section of distal bore 50. The width across a cross sectional slice of step 46 is one-half the difference in diameters between proximal bore 40 and the adjacent section of distal bore 50. Hub 34 is further formed so the inner wall 49 that defines middle bore 50 has a number of notches 48 (one identified) that extend outwardly from the inner wall of the hub that defines bore 50. Each notch 48 extends proximally from a location spaced distally from step 46 to the step. Each notch 48 is tapered in that the depth of the notch relative to the arcuately adjacent extends distally forward.

The hub body 36 is formed so that, extending distally forward of step 46, the diameter of first middle bore 50 gradually decreases. The distal end of the first middle bore 50 opens into a second middle bore 52. Second middle bore 52, like first middle bore 50 is tapered. The difference between the two bores is that the taper of second middle bore 52 is more pronounced than the taper of first middle bore 50. The second middle bore 52 opens into a distal bore 54. Distal bore 54 has a constant diameter and forms an opening at the distal end of hub 34.

Cannula tube 60, as implied by its name, is a tubular shaped member. Often tube 60 is formed from stainless steel. In many versions of the invention, tube 60 has an outer diameter that is 2.0 mm or less and more often 1.3 mm or less. A lumen 62 extends axially through the tube. Cannula 32 is assembled so that distal bore 54 opens into tube lumen 62. Typically the hub distal bore 54 has a diameter that is equal to or less than the diameter of tube lumen 62. While not illustrated in versions of the invention in which tube 60 is formed from conductive material an electrical insulator is disposed over most if not all of the tube. In some constructions of the invention, there is no insulator over the distal end tip of the tube 60. In the version of the tube 60 seen in FIG. 5A, the distal end of face of the tube is beveled. This facilitates the insertion of tube 60 through tissue.

Electrode 70, now described by reference to FIGS. 3 and 4, is part of an assembly that includes a cable 72. Cable 72 extends to a console (not illustrated) that serves as the source of current that is sourced to the patient using assembly 30 of this invention. One such console is the Applicant's Stryker MULTIGEN Console available from Stryker Instruments of Kalamazoo, Mich., United States. The structure of the console and cable 72 are not part of the present invention.

The cable 72 extends to a trunk 73 that can be considered the proximal most portion of the invention forming the electrode assembly 70. Trunk 73 is formed from a rigid plastic such as polyaryletherketone. Trunk 73 is cylindrical in shape. Electrode assembly 70 includes a head 74 that is integral with and extends distally forward from trunk 70. The head 74 is cylindrical in shape and has a diameter less than that of the trunk 70. Assembly 30 is constructed so that the outer diameter of electrode head 74 is approximately 0.1 mm less than the diameter of cannula proximal bore 40. This allows the close slip fitting of the electrode head 74 in the cannula bore 40. Head 74 is further formed to have a minimum diameter that is at least 0.2 mm greater than the maximum diameter of the cannula middle bore 50. This bore diameter is understood to be at least the diameter of the inner perimeter of step 46.

The electrode 70 is further formed so that at least one ear 76 extends radially outwardly from the outer cylindrical wall of the head. Electrode 70 is shaped so that when the head 74 is inserted in cannula proximal bore 40, the ear 76 will located forward of hub ribs 42. In the illustrated version of the invention, the electrode assembly 70 includes plural ears 76. Ears 76 are arcuately dimensioned and spaced apart from each other so that during the process of coupling the electrode assembly to the cannula each ear 76 can move between the annular gap in hub bore 40 between arcuately adjacent ribs 42. Head 74 is further understood to have a distally directed face 78.

An elongated conductive shaft 80 extends forward from the distal end face 78 of head 78. Shaft 80 is formed from electrically conductive material and is the actual component of the electrode 70 from which current is sourced and to which current is sunk. The components forming assembly 30 are designed so that when electrode 70 is properly seated in the cannula 32, the distal end tip of shaft 80 protrudes forward a short distance from the distal end opening of cannula tube 60. Not illustrated and not part of the application are the conductors internal to trunk 73 and head 74 that provide the electrical connection between a conductor internal to cable 72 and shaft 80.

Figure 6:
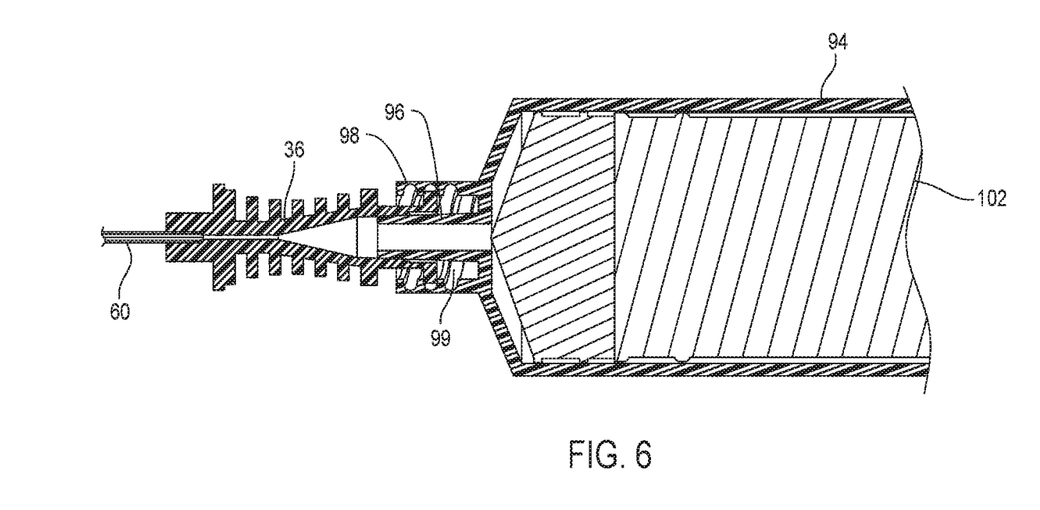
FIG. 6 is cross sectional view of the syringe coupled to the cannula.

Syringe 90, as seen in FIGS. 1 and 6, has an elongated tube like trunk or main section 94. Tabs 92 extend outwardly from opposed sides of the trunk 94 adjacent the proximal end of the trunk. A head 96 projects forward from trunk 94. The syringe 90 is formed so that as the head extends distally the outer diameter of the head 96 decreases. More particularly, the components forming assembly 30 are designed so that the distal most portion of syringe head will press against the inner wall of the cannula that defines the middle bore 50 and the portion of the syringe proximal to this section will be spaced from the inner wall 39 of cannula hub that defines proximal bore 40.

A collar 98 also extends forward from the distal end of syringe trunk 94. Collar 98 is circular in cross section surrounds and is radially spaced away from head 96. Collar 98 is formed with grooves 99 that extend outwardly from the inner surface of the collar. Grooves 99 extend in a helical pattern through collar 98.

A plunger 102 is slidably moved through and removed from the opening at the distal end of the syringe trunk.

Assembly 30 of this invention can be used for a nerve ablation procedure. When the assembly 30 is so used, cannula 32 is first inserted into the patient to provide a portal to a site that is adjacent the nerve to be ablated. During the cannula insertion process, a stylet is typically disposed in the bores and lumen that extend axially through the cannula (stylet not illustrated). The stylet provides structure strength to the cannula, especially tube 60. Once the cannula is so inserted, the stylet is removed.

The electrode 70 is then coupled to the cannula 32. In this process, the assembly shaft 80 is feed through proximal bore 40, middle bore 50 and distal bore 54 so as to extend in and through the cannula tube lumen 62. In this process, owing to the dimensioning of the components, the practitioner does not exert a relatively large force that would be needed overcome a friction (compression) force that holds the electrode head 74 static in the proximal bore 40. During the process of seating the cannula, the cannula 32 and electrode assembly 70 have a rotational orientation relative to each other that the electrode ears 76 can slide between the cannula ribs 42. The electrode assembly 70 is inserted into the cannula 34 until, owing to the above of the assembly components, electrode head face 78 seats against step 46 internal to the cannula. Step 46 functions as a stop that prevents further advancement of the electrode 70. Once assembly 30 is in this state, the distal end 81 of the electrode conductive shaft 80 projects out of cannula tube 60 as seen in FIG. 5A.

Figure 5:
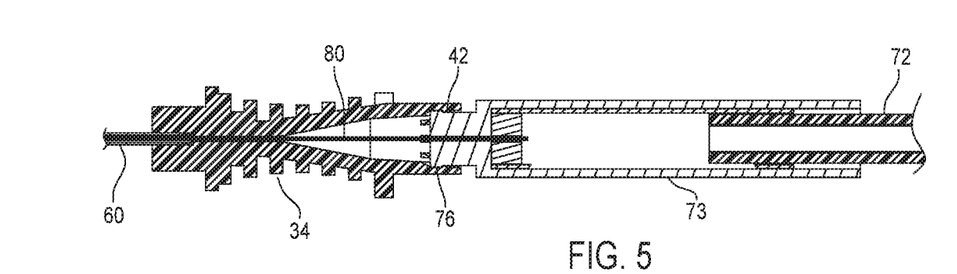
FIG. 5 is a cross sectional view of the electrode locked in the cannula.

Once the electrode 70 is so positioned, the assembly head 74 is rotated. The head is rotated so that each electrode rib 76 is in registration with and distal an associated one of the cannula ribs 42 as seen in FIG. 5. This positioning of the electrode 70 is considered to be the locking of the electrode assembly in place.

A low current, typically approximately 6 mAmps, is sourced to/sunk from the electrode. More particularly, this current is sourced from the tip of shaft 80 that extends out of cannula tube 60. The described version of the invention is a monopolar electrosurgical system. The current flows between the tip of electrode shaft 80 and a ground pad that is often adhesively secured to the patient. The ground pad is not part of the present invention and is not illustrated.

The practitioner monitors the reaction of the patient to this tissue. Based on the patient's reactions, the practitioner, by manipulating the exposed portion of the cannula 32, positions the cannula and electrode so that the exposed distal end of the electrode shaft 80 is in close proximity to the tissue to be ablated. Once this portion of the procedure is performed, the practitioner withdraws the electrode assembly 70. The withdrawal starts with the rotation of the electrode assembly so that ears 76 are rotated out of registration with cannula ribs 42. This is considered moving the electrode assembly from the locked state to the load state. Once the electrode 70 is in the load state, the electrode is withdrawn from the catheter 32.

The syringe 90 is filled with anesthetic. The syringe is then fitted coupled to the cannula 32. This process involves fitting the syringe over the cannula hub 34 so that each cannula tab 37 seats in a separate syringe groove 99. Syringe 90 is then rotated. Owing to the seating of cannula tabs 37 in syringe grooves 99, this rotation drives syringe head 96 into cannula bore 50. Owing to the dimensioning of the components, syringe head 96 presses against the inner wall of the hub that defines middle bore 50 as seen in FIG. 6. Owing to the nature of the material forming the components, this action results in the slight expansion of the cannula hub and/or the syringe head. The flexure of either or both of these components 34 and 96 forms an annular seal around the interface between these components.

By pressing the plunger 102 distally forward, the anesthetic is forced out through the distal end opening in the cannula tube 60. The anesthetic blocks the transmission of neurological signals, including pain signals, that can be generated in the next step. The syringe 90 is then removed. The syringe removal process is a reverse of the syringe coupling process.

To perform the actual nerve ablation, the electrode 70 is again coupled to the cannula. The same process used to couple and lock the electrode 70 to perform the stimulation procedure is used to lock the electrode in place at the start of the ablation procedure. Again current is source from/sunk to the end of the electrode shaft 80 that is located forward of cannula tube 60. This time the current sourced/sunk is at a higher level, typically between 400 and 700 mAmps. The resistance of the tissue to this current heats the nerve to the level where the cell forming the nerve ablates.

The electrode 70 is then withdrawn from the cannula. Cannula 32 is removed from the patient.

Assembly 30 of this invention is constructed so that when the electrode assembly is coupled to the cannula, the distal movement of the electrode is blocked by the abutment of the assembly head 74 against step 46 internal to the cannula. The dimensions of a single set of components forming the assembly are constant. This means that each time the electrode array is inserted in the same cannula the distal end 81 of the electrode shaft 80 projects essentially the same distance forward from the distal end of the cannula tube 60. This means that between the separate steps of the procedure, the stimulating step and the ablation step, even though the electrode assembly is removed and then reinserted into the cannula, assuming the position of the cannula is static, the position of the exposed end of the electrode shaft 80 likewise does not change. This invention minimizes the likelihood that, due to variations in the positioning of the electrode head 74 in the cannula hub 34, the position of the exposed distal end of the electrode shaft 80 likewise shift. Using this assembly 30, while maintaining the cannula 32 in a fixed position, means that the tissue targeted for ablation during the stimulating procedure is the tissue to which the ablating current is then applied.

Still another feature of this invention is that owing to the dimensioning of the components essentially minimal force, essentially a zero insertion force, is employed to insert the electrode 70 in the cannula 32 and to remove the electrode from the cannula. This reduces the extent to which the forces applied to the cannula 32 to remove the electrode assembly after the stimulating step and reinsert the electrode at the beginning of the ablation step can cause unintended movement of the cannula.

Likewise the simple rotation of the electrode assembly relative to the cannula moves the electrode between the locked and load states. The locking of the electrode 70 to the cannula 32 prevents the unintended decoupling of the electrode that could otherwise occur. Again owing to the design of this invention, only nominal force is applied to the cannula 32 and electrode 70 to move the electrode between the locked and unlocked states.

In addition to the above features, assembly 30 is designed so that when the syringe 60 is fitted to the cannula 32, a seal is formed between in the hub of the cannula around the head of the syringe. This ensures that the pressurized fluid, upon discharge from the syringe 90, flows towards the target tissue internal to the patient as opposed to leaking out of the proximal end of the cannula 32.

When the electrode 70 is fitted to the cannula, fluid may percolate through the cannula and lodge in the seat on cannula step 46. Notches 48 function as flow paths through which the fluid is able to gravity flow away from the step 46.

Figure 7:
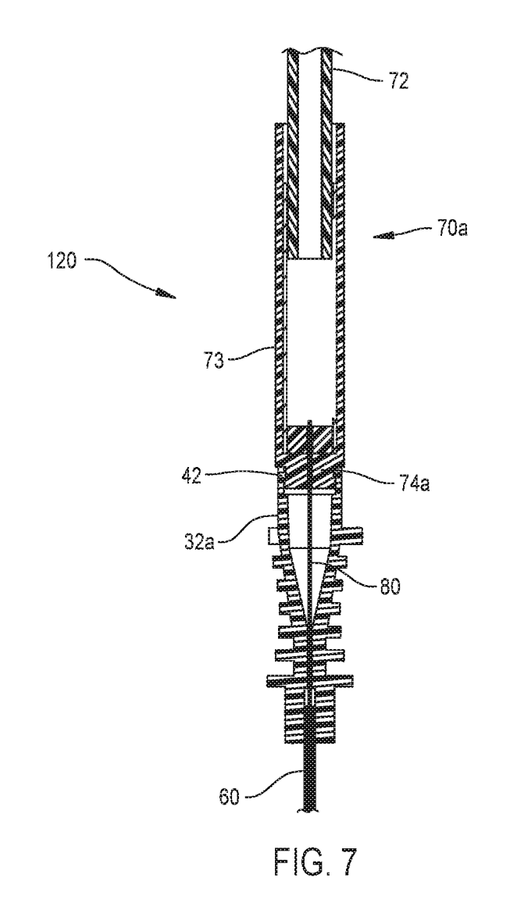
FIG. 7 is a cross sectional view of how in an alternative assembly of this invention, the electrode seats in the cannula.

FIG. 7 illustrates an alternative assembly 120 constructed in accordance with this invention. Assembly 120 includes an alternative cannula 32a and an alternative electrode 70a. While not illustrated in FIG. 7, it is understood that assembly 120 includes the previously described syringe 90.

Cannula 32a is substantially identical to the previously described cannula 32. The difference in the two cannulae 32 and 32a is that cannula 32a does not have the notches 48 incorporated into cannula 32.

Electrode 70a is essentially identical to electrode 70a. The difference between the electrodes 70 and 70a is that the proximal to distal length of the head 74a of electrode 70a is shorter than the length of the head of electrode 70. More specifically, electrode 70a is shaped so that when head 74a seats in cannula proximal bore 40, the distally directed face of head does not abut step 46.

Assembly 120 of this invention is thus designed so that when electrode 70a is coupled to cannula 32, the flat distally directed face of trunk 73, the face from which head 74a extends, abuts the proximally directed face of cannula hub main body 36. This is the annular face of the cannula hub that defines the opening into proximal bore 40. The face of trunk 73 also abuts proximally facing surfaces of the tabs 37 integral with the cannula hub 34. These surfaces of the cannula hub thus function as the stop surfaces that block the further advancement of the electrode 70a and, by extension, advancement of the electrode shaft 80.

As with the first assembly of this invention, syringe 90 is inserted in the cannula hub 34. When this event occurs, syringe head 96 presses against the surface of the hub that defines the middle bore 50 to form a seal between the cannula hub and the middle bore.

A benefit of assembly 120, is that when the practitioner sees the electrode trunk 73 pressing against the adjacent exposed faces of the cannula hub 34 the practitioner will visual notice that electrode 70a is in its distalmost position relative to cannula 32a.

Figure 8:
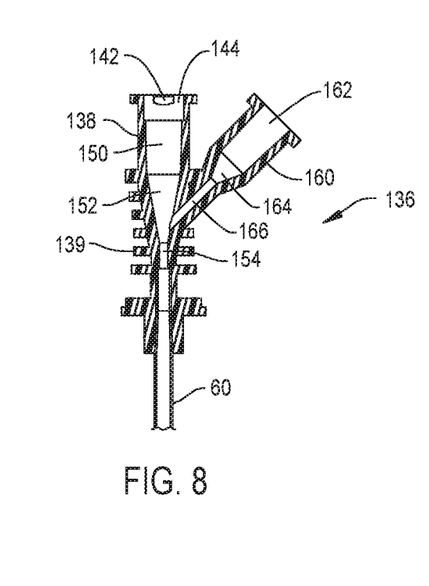
FIG. 8 is a cross sectional view of an alternative cannula of this invention.

FIG. 8 is illustrates the features of a cannula 136 of still another assembly of this invention. Cannula 136 includes a hub 138. Hub 138 has a main body 139. Tube 60 extends from the distal end of the main body. The hub main body 139 includes a first proximal bore 144 similar to bore 40. Proximal to bore 144 there is a first middle bore 150. First middle bore 150 is analogous in shape and function to bore 50. A step 146, similar to step 46 is located between bores 144 and 150. A second middle bore, bore 152, extends distally from bore 150. A constant diameter bore 154, similar to previously described bore 54, extends from the second middle bore 152. Bore 154 opens into tube 60.

Cannula hub 138 includes two ribs 142, one rib shown. Ribs 142, which are analogues to ribs 42, extend from the inner wall of the main body that defines the first proximal bore 144 so as to extend into the bore 144.

Cannula hub 138 includes a branch 160 that angles away from the main body 139 of the hub. In many versions of the invention, the branch 160 extends proximally rearward from the section of the hub main body 139 in which bore 152 is formed. In many but not all versions of the invention hub 138 is formed so that the angle between the longitudinal axis through the hub main body 139 and the longitudinal axis through branch 160 is an acute angle. At the proximal end of branch 160, the branch is shaped to have proximal bore, the second proximal bore 162 of the hub 138. Bore 162 is tapered such that extending distally from the proximal end of branch 160 the diameter of the bore 162 decreases. More particularly, the taper of bore 162 is such that the head 96 of syringe 90 can press against the inner wall of the hub 138 that defines the bore 138. The distal end of bore 162 opens into a transition bore, bore 164. Bore 164 has a taper such that, extending proximally, the diameter of bore 164 decreases at a greater change in diameter to length ratio than bore 162. The proximal end of bore 164 opens into a constant diameter conduit 166. Conduit 166 extends through hub branch 160. The distal end of conduit opens into the interior wall of the cannula main body 139 that defines bore 152.

Cannula 138 is inserted into the patient using the same methods used to insert cannulae 32 and 32a. An electrode 70 or 70a is inserted through bores 144, 150 and 152 so as to project out of the cannula tube 60. The engagement of the cannula ribs 142 with the electrode ears 76 removably holds the electrode 70 or 70a to the cannula. A stimulating current is sourced through the electrode 70 or 70a to find the nerve that is to be subjected to the ablation procedure.

Once the targeted tissue is located. The practitioner inserts the syringe 90 in second proximal bore 162. Owing to the cannula hub having two proximal bores 144 and 160, the practitioner does not have to remove the electrode 70 or 70a in order to couple the syringe to the cannula 136.

During the injection of the anesthetic into the tissue, some of the anesthetic may flow into, in order bores 152, 150 and 144. During this phase of the procedure, the electrode ears 76 and cannula ribs 142 continue to cooperate to releasably hold the electrode 70 or 70a to the cannula 136. Accordingly, there is essentially no likelihood that the fluid pressure of the anesthetic in the bores 144, 150 and 152 acting against the electrode 70 or 70a will cause the electrode to move relative to the cannula 136.

Cannula 136 of this invention thus allows the practitioner to introduce an anesthetic into the tissue to which the ablating current is to be applied without having to remove and the reattach the electrode to the cannula. This can reduce the time it takes to perform the procedure. Also since the electrode 70 or 70a is not removed between the stimulating step and the tissue ablation step, the likelihood the tip of the electrode will shift position relative to the cannula 136 between these two steps is further reduced.

The above is directed to specific versions of the assembly for sequentially applying an electrode to and introduce a fluid to a site located percutaneously within the patient. Other versions of this assembly may have features different from what has been described. Thus the features of the different versions of the invention can be combined.

For example, the cannula and electrode may have alternative complementary features for releasably holding the electrode in the proximal bore 40. One such set of features includes providing the one or both the cannula or electrode with a J-shaped slot. If the cannula 32 is provided with this slot/slots, the slot/slots is/are formed to project outwardly from the inner wall 39 of the cannula that defines bore 50. Thus the slot/slots is/are a recess/recesses in the inner wall of the cannula hub. The other component is provided with a tab/tabs that seat in the slot/slots. The insertion of the electrode seats the tab/tabs/in the slot/slots. Once the electrode 70 is seated, the electrode is rotated to seat the tab/tabs in the outer end of the slot/slots. This rotation thus places the electrode in the locked state relative to the cannula. An advantage of this version of the invention is that it ensures that when the electrode is locked in the cannula the shaft 80 is in a specific rotational orientation relative to the cannula tube 60. This may have benefits material to a specific use of the assembly of this invention.

Similarly the locking features integral with the cannula that protrude outwardly into the cannula bore 40 may have geometries different than those of the depicted ribs. For example the locking features may be a set of ramps and stops that protrude into the cannula bore. The electrode is formed with one or more complementary tabs. As a consequence of the electrode head being inserted in the cannula proximal bore 40, the abutment of the tabs against the cannula ramps and stops cause the rotation of the electrode head.

The outer shape of the cannula 32 is understood to not be a part of the present invention.

Further, there is no requirement that the cannula be formed so that step 46 is aligned on a plane perpendicular to the longitudinal axis that extends through the cannula. In other versions of the invention, this step may be a tapered step. This taper may be such that, extending distally through the hub, the diameter of the step decreases. Alternatively, this step may be such that extending proximally through the hub the diameter of the step decreases. In this version of the invention, step thus forms an annular void space that is located immediately forward of the outer perimeter of the electrode head 74. Generally, it should be understood that step 46 is a surface that is angularly offset from the adjacent proximal surface internal to the hub that defines the adjacent distal end of proximal bore 40. Step 46, in addition to being angularly offset from this surface is located radially inwardly from this adjacent proximal surface. Further, the surface forming step 46 is angularly offset from the adjacent distal surface that defines the adjacent proximal end of distal bore 50. Step 46, in addition to being angularly offset from this bore 50-defining surface is located radially outwardly from this surface.

In the preferred versions of the invention, step 46 is a surface that, relative to a line that is parallel to the longitudinal axis of the cannula and that extends proximally from outer edge of the step, is at an angle that is a maximum of 90° from this line.

In some versions of the invention, it may be desirable to seat a compressible washer on hub step 46. In these versions of the invention, essentially zero insertion force is used to initially seat the electrode head 74 in the cannula proximal bore 40. The complementary locking components are arranged so that the rotation of the electrode to perform the locking process drives the electrode head 74 against washer. This results in a compression of the washer so the washer functions as a seal between the cannula and the electrode. In this version of the invention, the ears 76 of the electrode head would thus be compressed between the washer and the complementary component of the cannula hub, for example, the ribs 42.

The dimensions, unless recited in the claims, are offered for purposes of specific applications of the invention.

Further, the described assembly is shown as being part of a conventional monopolar radiofrequency ablation system. The cannula and complementary electrode of this invention may have other shapes. For example, the Applicant's PCT Pat. App. No. PCT/US2013/027038, TISSUE ABLATION CANNULA AND ELECTRODE ASSEMBLY THAT CAN BE SELECTIVELY OPERATED WITH ONE OR MORE ACTIVE TIPS, filed 21 Feb. 2013, published as WO 2014/130031 A1, the contents of which are explicitly incorporated herein by reference, discloses the benefits of curving the cannula tube and electrode shaft. These features can be incorporated into the present application.

Likewise, there is no requirement that assembly only be used as part of a monopolar radiofrequency assembly. An alternative assembly of this invention may include a cannula and electrode designed to function as part of a bipolar radiofrequency assembly. In this type of assembly the cannula tube is formed to have a conductive surface that is separate from the conductive surface of the exposed tip of the electrode shaft. This is often accomplished by forming the tube as a set of overlapping tubes. The Applicant's PCT Pub. No. WO 2006/119245/U.S. Pat. No. 7,918,852, the contents of which are explicitly incorporated herein by reference, discloses one such design. Conductors extend from this surface back to the console over which the current is sourced. When this system is activated, the sourced current flows between the exposed tip of the electrode shaft and the exposed conductor integral with the cannula.

There is no requirement that in all versions of the invention, the cannula hub may be a single piece component. In some versions of the invention, the cannula hub 34 and tube 60 may be a single piece component.

Likewise, in alternative versions of the invention, a feature other than cannula may be formed with a feature other than step 46 that functions as a stop that prevents further advancement of the electrode. Thus feature may, for example, be a ring that protrudes into the proximal bore formed in the cannula. The ring may be formed of material that is flexible. Thus, when head of the electrode that presents a relatively large surface area to the ring, the resistance the ring imposes to the further insertion of the electrode functions as the tactile feedback that the practitioner should stop inserting the electrode. When a syringe, with a tapered nose, is inserted into the cannula. The surface area and taper of the syringe collectively causes the practitioner to employ a less force in order to overcome the resistance of the ring. In these versions of the invention the ring thus forms are seal between the cannula and the syringe.

In the above-described version of the invention, the proximally directed face of the ring is the equivalent of the step internal to the cannula hub. The ring surface that extends distally from this proximally facing surface defines the bore in which the head of the syringe is seated.

Likewise, there is no requirement that in all versions of the invention the cannula proximal bore, the bore in which the electrode head 74 is inserted by cylindrical in shape. In cross section the bore may be non-circular. In length, the diameter of the bore may vary along the longitudinal axis.

In some versions of the invention the bore immediately contiguous with proximal bore 40 may not be the bore dimensioned to receive head 96 integral with syringe 90. Thus, in some versions of the invention the proximal portion of the first middle bore 50, the section of the middle bare that partially defines step 46 may have a diameter that is constant along the proximal to distal longitudinal axis through the bore. In some versions of this invention this constant diameter middle bore 50 may have features designed to cooperate with complementary features integral with the syringe that facilitate the sealing and/or holding of the syringe to the cannula.

In versions of the invention with two proximal bores, the middle bore adjacent the proximal bore dimensioned to receive the electrode 70 or 70a may not be dimensioned to receive the head of the syringe 90. In these versions of the invention, the two proximal bores 144 and 162 may be parallel.

It is therefore the object of the appended claims to cover all such modifications that come within the true spirit and scope of this invention.

What is claimed is:

1. An assembly for performing an electrosurgical procedure, said assembly comprising:
   a cannula comprising:
      a cannula hub defining a proximal bore and a middle bore adjacent said proximal bore, said middle bore having a diameter smaller than a diameter of said proximal bore, wherein said cannula hub comprises at least one rib projecting radially inwardly within said proximal bore, and at least one tab projecting radially outwardly;
      a cannula tube coupled to and extending distally from said cannula hub, said cannula tube defining a lumen in fluid communication with said middle bore and said proximal bore;
   an electrode comprising:
      an electrode head configured to be removably inserted into said proximal bore of said cannula hub, said electrode head having an outer diameter smaller than said diameter of said proximal bore and greater than said diameter of said middle bore, wherein said electrode head comprises at least one ear projecting outwardly and configured to engage said at least one rib of said cannula hub with said electrode head removably inserted into said proximal bore to axially engage a distal end of said electrode head against said cannula hub;
      an electrode shaft coupled to and extending distally from said electrode head;
   a syringe comprising:
      a syringe trunk; and
      a syringe head configured to be removably inserted into said cannula hub, said syringe head coupled to and extending distally from said syringe trunk and having a length sufficient to extend past said proximal bore of said cannula hub and an outer diameter sized to engage said middle bore of said cannula hub, wherein said syringe head defines a groove configured to engage said at least one tab of said cannula hub to form an annular seal at an interface between said syringe head and said cannula hub.

2. The assembly of claim 1, wherein said cannula hub further comprises a step defining a transition surface between said proximal bore and said middle bore, wherein said step is configured to be engaged by said electrode head to prevent advancement of said electrode relative to said cannula when said electrode head is removably inserted into said proximal bore of said cannula hub.

3. The assembly of claim 2, wherein said cannula hub further comprises at least one notch within said step, said at least one notch configured to maintain fluid communication between said middle bore and said proximal bore when said electrode head is removably inserted into said proximal bore and engaging said step.

4. The assembly of claim 1, wherein said syringe head is formed from flexible materials such that expansion of said outer diameter of said syringe head is configured to facilitate said annular seal at said interface between said syringe and said cannula.

5. The assembly of claim 1, wherein said syringe further comprises a syringe collar coupled to and extending distally from said syringe trunk and radially spaced outwardly from said syringe head, wherein said cannula hub further comprises a locking feature configured to releasably engage said syringe collar.

6. The assembly of claim 5, wherein said syringe collar defines a groove, and wherein said locking feature is a tab.

7. The assembly of claim 5, wherein said locking feature is a first locking feature, said cannula hub further comprising a second locking feature configured to releasably engage said electrode head when said electrode head is removably inserted into said proximal bore of said cannula hub.

8. The assembly of claim 7, wherein said second locking feature is a rib within said proximal bore, and wherein said electrode head further comprises an ear configured to releasably engage said rib.

\* \* \* \* \*